(12) United States Patent
Reghabi et al.

(10) Patent No.: US 8,948,836 B2
(45) Date of Patent: Feb. 3, 2015

(54) IMPLANTABLE APPARATUS FOR SENSING MULTIPLE PARAMETERS

(75) Inventors: Bahar Reghabi, Marina Del Ray, CA (US); Rebecca K. Gottlieb, Culver City, CA (US); Rajiv Shah, Rancho Palos Verdes, CA (US); Bradley J. Enegren, Moorpark, CA (US); William P. Van Antwerp, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 2498 days.

(21) Appl. No.: 10/746,129

(22) Filed: Dec. 26, 2003

(65) Prior Publication Data

US 2005/0148832 A1 Jul. 7, 2005

(51) Int. Cl.
| | |
|---|---|
| *A61B 5/145* | (2006.01) |
| *A61B 5/1473* | (2006.01) |
| *A61B 5/1468* | (2006.01) |
| *A61B 5/1486* | (2006.01) |

(Continued)

(52) U.S. Cl.
CPC ............. *A61B 5/14865* (2013.01); *A61B 5/01* (2013.01); *A61B 5/0215* (2013.01); *A61B 5/14532* (2013.01); *A61B 5/14539* (2013.01); *A61B 5/14546* (2013.01); *A61B 5/1459* (2013.01); *A61B 5/412* (2013.01); *A61B 5/4839* (2013.01); *A61B 5/6852* (2013.01); *A61B 5/14542* (2013.01); *A61B 5/14551* (2013.01); *A61B 2562/063* (2013.01)
USPC ........... 600/345; 600/500; 600/347; 600/365; 600/309; 600/355; 600/485; 600/561; 600/481

(58) Field of Classification Search
CPC .............. A61B 5/145; A61B 5/14503; A61B 5/14532; A61B 5/14542; A61B 5/1468; A61B 5/1473; A61B 5/14735; A61B 5/1486; A61B 5/14865; A61B 5/1495; A61B 5/01; A61B 5/0215; A61B 5/14539; A61B 5/14546; A61B 5/412; A61B 5/4839; A61B 5/6852; A61B 5/14551; A61B 2562/063
USPC ......... 600/309, 345–366, 301, 481, 485, 500, 600/561
See application file for complete search history.

(56) References Cited

U.S. PATENT DOCUMENTS

| | | | |
|---|---|---|---|
| 4,020,830 A | * | 5/1977 | Johnson et al. ............... 600/348 |
| 4,703,156 A | | 10/1987 | Hayes |

(Continued)

FOREIGN PATENT DOCUMENTS

| | | |
|---|---|---|
| WO | WO-02/102267 A1 | 12/2002 |
| WO | WO 02/102267 A1 | 12/2002 |

OTHER PUBLICATIONS

PCT International Search Report as issued in International Application No. PCT/US04/041932, Mailing date Mar. 31, 2005.

(Continued)

*Primary Examiner* — Navin Natnithithadha
(74) *Attorney, Agent, or Firm* — Medtronic MiniMed, Inc.

(57) ABSTRACT

An apparatus for sensing multiple parameters includes an implantable housing and a plurality of implantable sensors disposed within the implantable housing. The plurality of implantable sensors sense parameters in a patient, such as biological or physiological parameters, for example, and each responds to an analyte in the patient. The plurality of implantable sensors may include, but is not limited to, electrochemical, potentiometric, current and optical sensors.

24 Claims, 9 Drawing Sheets

(51) Int. Cl.

| | |
|---|---|
| *A61B 5/02* | (2006.01) |
| *A61B 5/024* | (2006.01) |
| *A61B 5/021* | (2006.01) |
| *A61B 5/0215* | (2006.01) |
| *A61B 5/01* | (2006.01) |
| *A61B 5/1459* | (2006.01) |
| *A61B 5/00* | (2006.01) |
| *A61B 5/1455* | (2006.01) |

(56) References Cited

U.S. PATENT DOCUMENTS

| | | | |
|---|---|---|---|
| 4,703,756 A | 11/1987 | Gough et al. | |
| 5,207,103 A * | 5/1993 | Wise et al. | 73/724 |
| 5,651,767 A * | 7/1997 | Schulman et al. | 604/8 |
| 5,711,861 A * | 1/1998 | Ward et al. | 600/347 |
| 5,999,848 A | 12/1999 | Gord et al. | |
| 6,088,608 A * | 7/2000 | Schulman et al. | 600/345 |
| 6,175,752 B1 * | 1/2001 | Say et al. | 600/345 |
| 6,212,416 B1 * | 4/2001 | Ward et al. | 600/345 |
| 6,248,067 B1 | 6/2001 | Causey, III et al. | |
| 6,259,937 B1 * | 7/2001 | Schulman et al. | 600/345 |
| 6,387,048 B1 * | 5/2002 | Schulman et al. | 600/300 |
| 6,405,066 B1 * | 6/2002 | Essenpreis et al. | 600/347 |
| 6,477,395 B2 * | 11/2002 | Schulman et al. | 600/345 |
| 6,498,043 B1 * | 12/2002 | Schulman et al. | 438/1 |
| 6,516,808 B2 * | 2/2003 | Schulman | 128/899 |
| 6,560,471 B1 * | 5/2003 | Heller et al. | 600/347 |
| 6,565,509 B1 * | 5/2003 | Plante et al. | 600/345 |
| 6,770,030 B1 * | 8/2004 | Schaupp et al. | 600/309 |
| 6,931,327 B2 * | 8/2005 | Goode, Jr. et al. | 702/22 |
| 6,952,604 B2 * | 10/2005 | DeNuzzio et al. | 600/345 |
| 6,990,366 B2 * | 1/2006 | Say et al. | 600/345 |
| 7,003,341 B2 * | 2/2006 | Say et al. | 600/345 |
| 7,079,881 B2 * | 7/2006 | Schulman et al. | 600/347 |
| 7,146,203 B2 * | 12/2006 | Botvinick et al. | 600/345 |
| 7,162,289 B2 * | 1/2007 | Shah et al. | 600/345 |
| 7,190,988 B2 * | 3/2007 | Say et al. | 600/345 |
| 7,276,029 B2 * | 10/2007 | Goode, Jr. et al. | 600/365 |
| 7,366,556 B2 * | 4/2008 | Brister et al. | 600/347 |
| 7,426,408 B2 * | 9/2008 | DeNuzzio et al. | 600/345 |
| 2001/0039374 A1 * | 11/2001 | Schulman | 600/300 |
| 2003/0050547 A1 | 3/2003 | Lebel et al. | |
| 2003/0100821 A1 * | 5/2003 | Heller et al. | 600/347 |

OTHER PUBLICATIONS

Mathias ,JR, Sninsky CA, Millar HD, Clench MH, Davis RH. Development of an Improved Multi-Pressure-Sensor Probe for Recording Muscle Contraction in Human Intestine. Digestive Diseases and Sciences, vol. 30, No. 2 (Feb. 1985), pp. 119-123. Germany.

Latham RD, Westerhof N, Sipkema P, Rubal BJ, Reuderink P, Murgo JP. Regional wave travel and reflections along the human aorta: a study with six simultaneous micromanometric pressures. Circulation 72, No. 6, 1257-1 269, 1985. USA.

Brooke Army Medical Center (BAMC) Catheterization Records 1985-1992 (includes records from 1975 and 1973), San Antonio, Texas.

Millar Instruments Mikro-Tip® Catheter Pressure Transducers and Accessories Product Information, Feb. 1, 1985, Houston, Texas.

Codman (Johnson & Johnson) product brochure, IOP Express http://www.codmanjnj.com/PDFs/Icp_i-98.pdf, USA.

Codman® (Johnson & Johnson) ICP Monitoring System Quick Set-Up Guide http://www.codmanjnj.com/PDFs/Icp_i-99 .pdf, USA.

Millar Mikro-tip(R) Catheter Pressure Transducers Product Information and.Price List, Jan. 1, 1984, Houston, Texas.

Millar Mikro-tip(R) Catheter Transducers product brochure, pp. 2 and 3, Houston, Texas.

Office Action dated May 25, 2010 from related Japanese application No. 2006-547119.

Jobst et al., "Thin-film Microbiosensors for Glucose-Lactate Monitoring", Anal. Chem. 1996, 68, 3173-379.

Decision on Appeal dated Nov. 12, 2009 from related EP patent application No. 04814151.9.

Office Action dated Dec. 19, 2006 from related EP patent application No. 04814151.9.

Office Action dated May 30, 2008 from related EP patent application No. 04814151.9.

Search Report dated Mar. 31, 2005 from related PCT application No. PCT/US2004/041932.

* cited by examiner

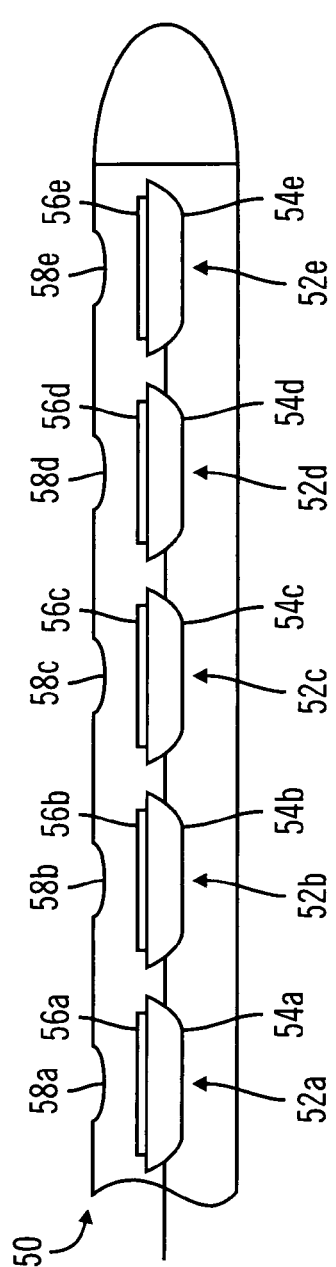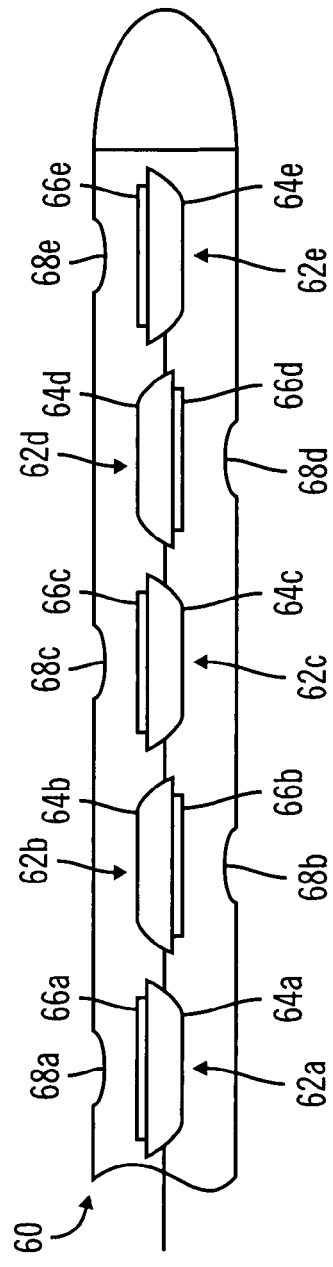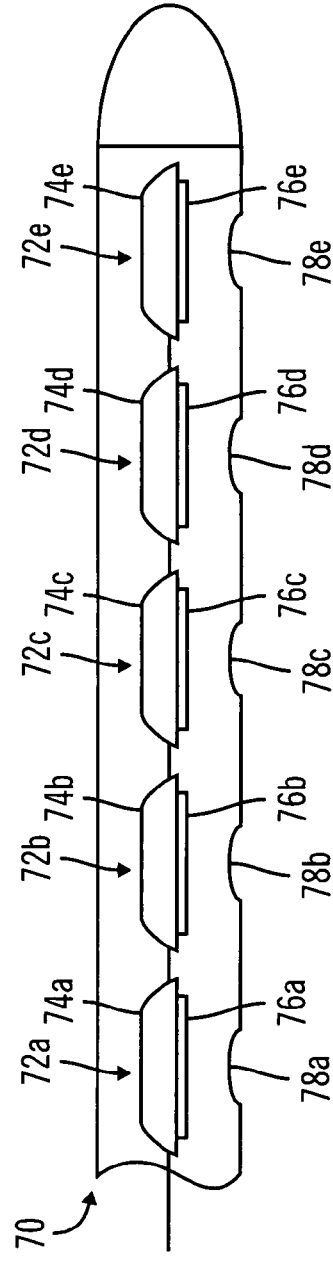

IMPLANTABLE APPARATUS FOR SENSING MULTIPLE PARAMETERS

BACKGROUND

1. Field of the Invention

Embodiments of the present invention relate to biomedical sensor technology and, in particular, to implantable apparatuses for sensing multiple parameters in a patient.

2. Description of Related Art

The ability to monitor biological or physiological parameters, analytes and other parameters in a patient in emergency rooms, intensive care units and other hospital settings is critical in stabilizing patients and reducing mortality rates. The monitoring of blood oxygen saturation, blood pressure, glucose, lactate, temperature, potassium and pH, for example, provides an indication of the state of tissue oxygen balance in the patient, knowledge of which is crucial in preventing a patient from progressing toward a serious, debilitating medical condition or even death.

Various situations require prompt monitoring and response to a change in body chemistry or other patient parameters. For example, sepsis, a toxic condition resulting from the spread of bacteria or their products from a focus of infection, can lead to global tissue hypoxia, multiple organ failures, cardiovascular collapse and eventual death. Increased blood lactate concentrations and decreased mixed venous oxygen saturation are classic indicators of the early phases of septic shock. By monitoring these parameters, blood chemistry levels can be regulated and the incidence of severe sepsis and septic shock decreased.

The prevention of severe sepsis and septic shock has become increasing important. Cases of sepsis occur more frequently in elderly persons than in younger populations. As the number of elderly persons continues to increase, the number of cases of severe sepsis and septic shock can be expected to increase as well.

Blood glucose is another parameter that requires monitoring in a medical setting in order to maintain proper levels in a patient and reduce mortality rates. For example, for patients who are in an intensive care environment, especially those with diabetes, glucose monitoring is critical. If the amount of glucose in the diabetic patient's system is not maintained at proper levels, the patient may sustain serious or life-threatening injury. If too much glucose accumulates in the diabetic patient's system, the patient could become hyperglycemic, resulting in shortness of breath, nausea and vomiting at best or diabetic coma and death in the worst case. If there is too little glucose in the diabetic patient's system, the patient could become hypoglycemic, resulting in dizziness, sweating and headache at best and unconsciousness and death in the worst case.

As another example, the medical community has a demonstrated need to understand the local pressure and oxygen, glucose and lactate concentrations in the brain following traumatic injury or stroke. However, typical techniques for measuring pressure and metabolic analytes in the brain requires three catheters and three holes drilled into the cranium to provide pathways for the catheters. One catheter is used to measure pressure, a second catheter is used to measure $O_2$, pH and $pCO_2$, and a third catheter is a microdialysis catheter used to measure glucose and lactate. Each catheter requires its own control electronics and data monitoring systems. Clearly, a measurement system of this type is cumbersome at best.

Traditionally, the monitoring of patient parameters in a hospital or other medical setting has been accomplished by drawing a blood sample and sending the sample to a laboratory for analysis. This type of monitoring process, while well-established and providing accurate results, is time-consuming and, indeed, time-prohibitive in an emergency situation. By the time lab results return to an attending physician, the patient may have already entered into a serious state or even may have already died.

Some industry attempts have been made to provide continuous, immediate monitoring of patient parameters. For example, Diametrics Medical, Inc., has developed several sensing systems, such as the NEUROTREND Sensor and the PARATREND7+ Sensors. The NEUROTREND Sensor is a disposable, single-use device for the continuous measurement of intracranial pH, $pCO_2$, $pO_2$, and temperature that is used in conjunction with an appropriate intracranial access device. The device incorporates optical sensors for the measurement of pH, $pCO_2$, and $pO_2$, and a thermocouple for temperature measurement. The NEUROTREND sensor indicates the perfusion and metabolic acidosis/alkalosis status of cerebral tissue in the vicinity of the sensor. The PARATREND7+ Sensors are disposable, single-use fiberoptic devices for continuous measurement of pH, $pCO_2$, $pO_2$ and temperature, providing real-time oxygenation, ventilation and metabolic information for critically ill patients.

However, the NEUROTREND Sensors and the PARATREND7+ Sensors have limited capabilities. Optical sensors lose effectiveness quickly when proteins deposit on their surface, which is inevitable in the body. The NEUROTREND Sensors and the PARATREND7+ Sensors, which are based on optical sensors, thus, tend to lose their effectiveness quickly. Accordingly, medical professionals must still use conventional techniques for obtaining reliable, quantifiable parameter values in addition to the values indicated by the NEUROTREND Sensors and the PARATREND7+ Sensors when administering to patients.

To date, there have been no implantable sensors providing continuous, quantifiable, simultaneous measurement values for patient parameters. In particular, there have been no implantable sensors providing continuous, quantifiable, simultaneous measurement values for lactate, glucose, pH, temperature, venous oxygen pressure, venous oxygen concentration and potassium. An implantable, multi-parameter sensor that monitors one or more of glucose, lactate, pH, temperature, venous oxygen pressure, venous oxygen concentration and blood potassium could be used advantageously in hospital or medical settings, in critical care, emergency care and intensive care situations, in triage, surgery and in field applications. For example, because a patient's blood glucose concentration may increase during kidney dialysis, the monitoring of glucose, oxygen and temperature during dialysis may be helpful.

SUMMARY

It is therefore an object of embodiments of the present invention to provide an apparatus for sensing multiple parameters in a patient. It is a further object of embodiments of the present invention to provide a sensing apparatus that responds to a plurality of analytes simultaneously. It is yet a further object of embodiments of the present invention to provide an apparatus for sensing multiple parameters that can be used in critical care, intensive care or emergency environments. It is yet a further object of embodiments of the present invention to provide an apparatus for sensing multiple parameters that can provide continuous measurement of blood oxygen saturation and lactate.

An apparatus for sensing multiple parameters may include an implantable housing; an implantable tip affixed to a first end of the housing; and a plurality of implantable sensors disposed within the implantable housing for sensing parameters in a patient. Each of the plurality of implantable sensors may respond to a parameter in the patient.

At least one of the plurality of implantable sensors may be a biological parameter sensor, a physiological parameter sensor, an electrochemical sensor, a potentiometric sensor, a current sensor or an optical sensor. Also, at least one of the plurality of implantable sensors may produce an analog output or a digital output.

The plurality of implantable sensors may be wired together in a daisy-chain configuration or may be wired independently from one another. Also, at least two of the plurality of implantable sensors may be wired together in a daisy-chain configuration or may be wired independently from one another.

At least one of the plurality of implantable sensors may respond to blood oxygen saturation, glucose, lactate, temperature, potassium or pH. At least one of the plurality of implantable sensors may include an electrode. The parameter may be a biological parameter, a physiological parameter or an analyte.

The tip may be an ogive-shaped tip. The housing may be silicone. The housing may also be a catheter or a multi-lumen catheter. The apparatus may further include an infusion line for delivering an infusant disposed within the implantable housing and adjacent the plurality of sensors.

An implantable sensor may include an implantable housing; an implantable tip affixed to a first end of the housing; and a plurality of implantable sensing elements disposed within the implantable housing for sensing parameters in a patient. The plurality of implantable sensing elements may be biological parameter sensing elements. The plurality of implantable sensing elements may be physiological parameter sensing elements. The plurality of implantable sensing elements may be analyte sensing elements.

At least one of the plurality of sensing elements responds to blood oxygen saturation. Also, the sensor may further include an infusion line for delivering an infusant. The infusion line may be disposed within the implantable housing and adjacent the plurality of sensing elements.

A method of fabricating apparatus for sensing multiple parameters may include providing a plurality of implantable sensors; and enclosing the plurality of implantable sensors in an implantable housing. The plurality of implantable sensors may be biological parameter sensors or physiological parameter sensors. The plurality of implantable sensors may be analyte sensors. The method may further include enclosing an infusion line in the implantable housing.

BRIEF DESCRIPTION OF THE DRAWINGS

FIG. 3a shows a cross-sectional view of another apparatus for sensing multiple parameters according to an embodiment of the present invention.

FIG. 3b shows a cross-sectional view of another apparatus for sensing multiple parameters according to an embodiment of the present invention.

FIG. 3c shows a cross-sectional view of another apparatus for sensing multiple parameters according to an embodiment of the present invention.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Although the following description is directed primarily toward apparatuses for sensing multiple parameters in a patient, embodiments of the present invention may be used in a variety of capacities and applications. For example, embodiments of the present invention may be used for critical care, intensive care or emergency environments. Also, embodiments of the present invention may be used in hospitals to simultaneously measure multiple analytes. Generally, embodiments of the present invention may be adapted for use in any type of medical or hospital situation where simultaneous measurement of biological or physiological parameters or analytes is desired.

Figure 1:
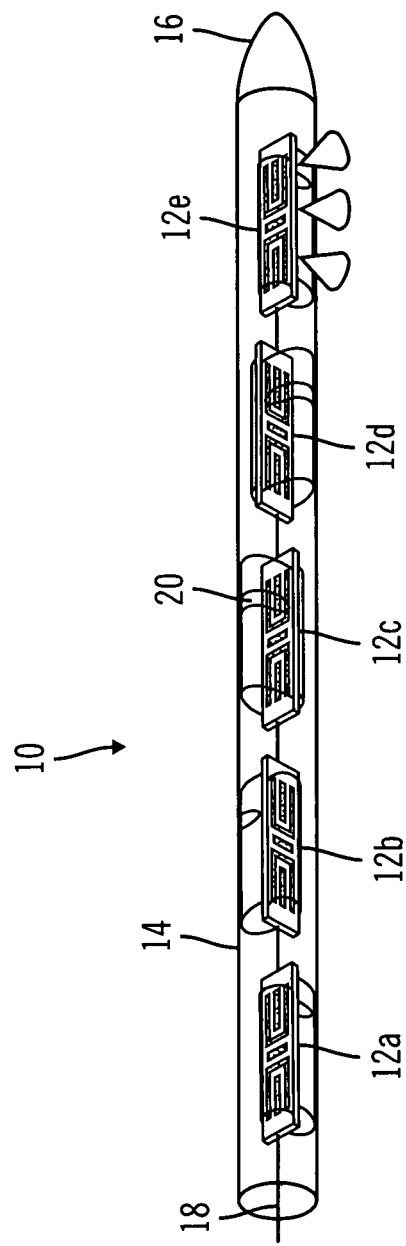
FIG. 1 shows a perspective view of an apparatus for sensing multiple parameters according to an embodiment of the present invention.

An apparatus for sensing multiple parameters 10 according to an embodiment of the present invention may be seen in FIG. 1. The apparatus for sensing multiple parameters 10 shown in FIG. 1 includes, but is not limited to, a housing 14, a plurality of sensors 12a-12e, a tip 16 and an interconnect 18. The housing 14 may also include one or more apertures 20 for permitting physical or other contact between fluids in the body and sensing elements located on each of the plurality of sensors 12a-12e.

Each of the plurality of sensors 12a-12e may be designed to sense one or more parameters. For example, each of the plurality of sensors 12a-12e may be designed to sense a biological or physiological parameter in a patient, such as, for example, blood oxygen saturation, blood pressure, blood temperature, or blood pH. Also, each of the plurality of sensors 12a-12e may be designed to sense a parameter such as an analyte in a patient, such as, for example, glucose, lactate, or potassium. Accordingly, given the various mechanisms required to sense various parameters, each of the plurality of sensors 12a-12e may be designed as an electrochemical sensor, a potentiometric sensor, a current sensor, a physical quantity sensor, an optical sensor or other type of sensor, dictated by the parameter being measured.

Figure 5:
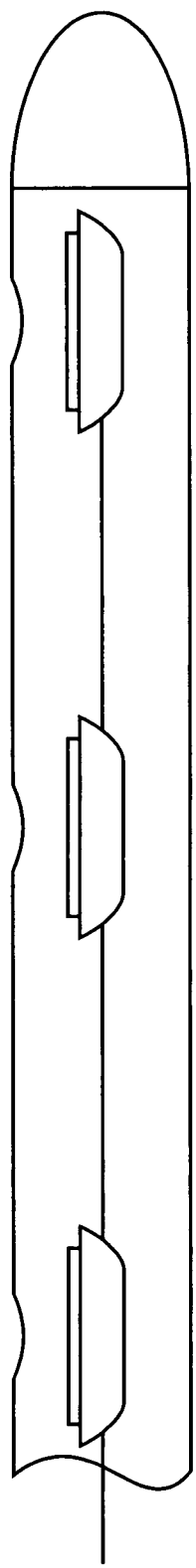
FIG. 5 shows a cross-sectional view of another apparatus for sensing multiple parameters according to an embodiment of the present invention.

Although the embodiment of the present invention shown in FIG. 1 includes five sensors, embodiments of the present invention may be designed with any number of sensors desired or necessary for a particular application. For example, an embodiment of the present invention shown in FIG. 5 includes, without limitation, three sensors.

The plurality of sensors 12a-12e shown in FIG. 1 are "daisy-chained" together via the interconnect 18. Because "daisy-chaining" modules is facilitated by digital addressing, each of the plurality of sensors 12a-12e shown in the embodiment of FIG. 1 includes an analog-to-digital (A/D) converter integrated circuit as well as a power supply for powering the integrated circuit, such as, for example, a capacitor. Thus, because each of the plurality of sensors 12a-12e includes an onboard A/D, the information leaving the housing 14 on the interconnect 18 is in digital form.

Also, each of the plurality of sensors 12a-12e may be individually addressed by a remote device, such as, for example, a computer or other controller. The addressing schemes may be any scheme common in the industry and may include, without limitation, various modulation schemes such as frequency modulation or time modulation schemes, for example.

The housing 14 may be fabricated in a variety of ways. For example, the housing 14 may be a single, standard catheter that is flexible for vascular placement. If the housing 14 is a flexible catheter, the apparatus for sensing multiple parameters 10 may be placed independently in the body. In addition, the housing 14 may be one lumen of a multi-lumen catheter or may be part of a central venous line or sheath. According to an embodiment of the present invention, the housing 14 may be made of silicone or a polyethylene, for example.

According to an embodiment of the present invention, the tip 16 may be an ogive shape, i.e., a "bullet nose." An ogive-shaped tip 16 may optimize a flow field around the apparatus for sensing multiple parameters 10 and, being curved, may be less likely to gouge the patient during insertion. According to another embodiment of the present invention, the tip 16 may have some sort of structure, such as, for example, a screw anchor or other structure, allowing it to be fixed into tissue.

Figure 2:
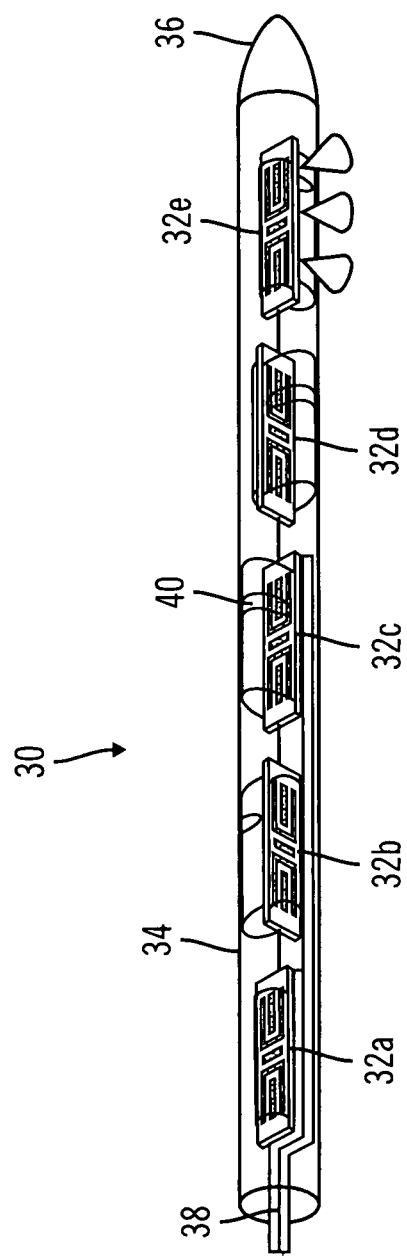
FIG. 2 shows a perspective view of another apparatus for sensing multiple parameters according to an embodiment of the present invention.

FIG. 2 shows an apparatus for sensing multiple parameters 30 according to another embodiment of the present invention. The apparatus for sensing multiple parameters 30 includes, but is not limited to, a plurality of sensors 32a-32e, a housing 34, a tip 36 and an interconnect 38. The housing 34 may also include one or more apertures 40 allowing fluids in the body to come into physical contact with the sensors 32a-32e.

Whereas each of the plurality of sensors 12a-12e of FIG. 1 were daisy-chained together, the plurality of sensors 32a-32e in FIG. 2 operate independently of one another and are individually wired. In other words, according to the embodiment of the present invention shown in FIG. 2, each of the plurality of sensors 32a-32e has a wire connected to it that is routed out of the housing 34 such that the interconnect 38 is actually a plurality of interconnects. Because there is no daisy-chain configuration in the embodiment of the invention shown in FIG. 2, there is no need for each of the plurality of sensors 32a-32e to be digitally addressable. Each of the plurality of sensors 32a-32e may transmit or receive an analog signal; there is no requirement to include an onboard A/D integrated circuit and associated power supply. Without the A/D integrated circuit and associated power supply, the "wired" sensing apparatus 30 according to the embodiment of the present invention shown in FIG. 2 may have a reduced size, making it flexible and desirable for medical and/or surgical use.

Embodiments of the present invention need not be limited to a "daisy-chained" sensing apparatus as shown in FIG. 1 or a "wired" sensing apparatus as shown in FIG. 2. Embodiments of the present invention may also include, without limitation, a combination of daisy-chained and wired configurations.

The sensors 12a-12e and 32a-32e shown in the embodiments of the invention of FIG. 1 and FIG. 2 may be physically disposed in a variety of ways. For example, the plurality of sensors 12a-12e shown in FIG. 1 and the plurality of sensors 32a-32e shown in FIG. 2 are arranged in a "perpendicular" fashion. In other words, in the embodiments of the invention shown in FIGS. 1 and 2, each sensor is aligned perpendicularly or is "on its side" relative to the sensor adjacent to it. Thus, according to embodiments of the present invention, flexibility in position and/or orientation may be achieved. For example, according to embodiments of the present invention, a drug may be dosed in a perpendicular fashion on one half of the catheter while a parameter may be measured on another half of the catheter. Also, in embodiments of the invention in which all sensing elements are disposed on one side or the catheter, for example, the catheter may be rotated or positioned in multiple orientations to determine a variance in readings for a particular environment, thus indicating whether an environment is "well-mixed."

FIG. 3A shows another embodiment of the present invention having a plurality of sensors 52a-52e all aligned in a first orientation. In the embodiment of the invention shown in FIG. 3A, all sensor substrates 54a-54e face in the same direction. Likewise, all sensing elements 56a-56a also face in the same direction. To accommodate the sensing elements 56a-56e, the housing of the apparatus for sensing multiple parameters 50 may also include apertures 58a-58e which allow fluids to make physical contact with the sending elements 56a-56a.

The physical placement of sensors according to another embodiment of the present invention may be seen in FIG. 3B. In FIG. 3B, an apparatus for sensing multiple parameters 60 includes, but is not limited to, a plurality of sensors 62a-62a. Sensor substrates 64a, 64c, and 64e face in a direction opposite that of sensor substrates 64b and 64d. Likewise, a first sensing element 66a, a second sensing element 66c and a third sensing element 66e face in a direction opposite that of a fourth sensing element 66b and a fifth sensing element 66d. The housing of the apparatus for sensing multiple parameters 60 may include apertures 68a-66e which allow fluids to make physical contact with the sensing elements 66a-66e.

FIG. 3C shows sensing elements aligned in another configuration according to an embodiment of present the invention. In FIG. 3C, each of the plurality of sensors 72a-72e are aligned in the same direction. However, each of the sensors 72a-72e are aligned in a direction opposite the sensors 52a-52e shown in FIG. 3A. Also, in the embodiment of the invention shown in FIG. 3C, the apparatus for sensing multiple parameters 70 includes apertures 78a-78a which allow fluids to make physical contact with the sensing elements 76a-76a.

Figure 4:
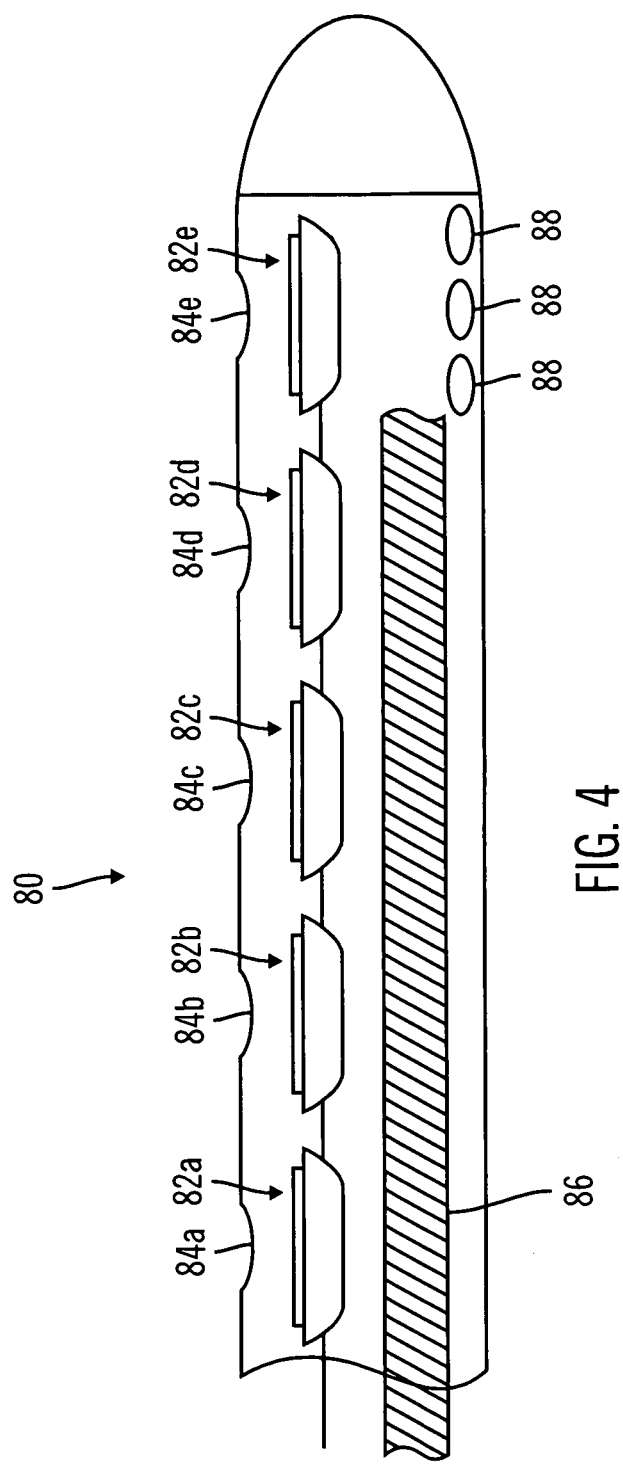
FIG. 4 shows a cross-sectional view of another apparatus for sensing multiple parameters according to an embodiment of the present invention.

An apparatus for sensing multiple parameters 80 according to yet another embodiment of present the present invention is shown in FIG. 4. The apparatus for sensing multiple parameters 80 includes, but is not limited to, a plurality of sensors 82a-82a, a plurality of sensor apertures 84a-84e, an infusion line 86 and infusion apertures 88. The apparatus for sensing multiple parameters 80 also includes a housing 81 and a tip 83.

In the embodiment of the invention shown in FIG. 4, the infusion line 86 allows an infusant, drug or other medicant to be delivered to a patient through the infusion apertures 88. Thus, if an analyte sensed by the sensors 82a-82e indicates that it would be advantageous for a patient to be treated with an infusant, the infusant may be delivered directly through the infusion line 86 and through the infusion apertures 88 to the patient. The apparatus for sensing multiple parameters 80 according to the embodiment of the invention shown in FIG. 4 eliminates the need to insert an additional catheter into the patient for delivery of an infusant.

According to embodiments of the present invention, the sensors used for sensing parameters in a patient, such as, for example, sensors 12a-12e shown in FIG. 1, may sense one or more biological or physiological parameters or one or more analytes. For example, referring back to FIG. 1, the first sensor 12A may be a glucose sensor using a glucose oxidase enzyme capable of measuring glucose and oxygen concentration. The first sensor 12a may be an electrochemical sensor. A sensor of this type is disclosed in a patent application entitled "Sensing Apparatus and Process," Ser. No. 10/036,093, filed Dec. 28, 2001, the contents of which are hereby incorporated by reference herein. A substrate that may be used for the first sensor 12A is disclosed in a patent application entitled "Sensor Substrate and Method of Fabricating Same," Ser. No. 10/038,276, filed Dec. 28, 2001, the contents of which are hereby incorporated by reference herein. The first sensor 12a may also include a thermistor for measuring temperature.

The second sensor 12b shown in FIG. 1 may be designed to sense lactate, temperature and oxygen pressure. The second sensor 12b may be an electrochemical sensor. The second sensor 12b may be a modification of the first sensor 12a. For example, according to an embodiment of the present invention, if the first sensor 12a uses a glucose oxidase enzyme to effect glucose measurements, the second sensor 12b may use a similar sensor and replace the glucose oxidase enzyme with a lactose oxidase enzyme to effect lactate measurements.

The third sensor 12c shown in FIG. 1 may be designed to sense potassium while the fourth sensor 12d shown in FIG. 1 may be designed to sense pH. The third sensor 12c and the fourth sensor 12d may be potentiometric sensor.

Oxygen saturation may be derived from other parameters, such as pH, $pO_2$ and temperature, for example, or may be measured directly. The fifth sensor 12e shown in FIG. 1 may be designed as an oximeter and may be capable of measuring oxygen saturation levels. Thus, the fifth sensor 12e may be an optical sensor or a pulse oximeter ($SvO_2$ or $SpO_2$). According to another embodiment of the present invention, the fifth sensor 12e may be a co-oximeter. A co-oximeter may be used in direct contact with the blood. A co-oximeter may utilize four wavelengths of light to separate oxyhemoglobin from reduced hemoglobin, methemoglobin (MetHb) and carboxyhemoglobin (COHb). Pulse oximeters may measure COHb and part of any MetHb along with oxyhemoglobin measurements. A substrate for a sensor may be designed to effect a co-oximeter. For example, the substrate disclosed in the patent application entitled "Sensor Substrate and Method of Fabricating Same," Ser. No. 10/038,276, may be modified such that it can accommodate measuring four wavelengths of light. Four vias of the substrate may be fabricated using glass, polycarbonate, or any other material that can pass the desired wavelengths, each via being capable of passing one wavelength.

The sensor may also be fabricated with a light-emitting diode (LED) designed into it. By incorporating an LED into the sensor, blood oxygen saturation may be determined by monitoring the various wavelengths reflected from the blood using light emanating from the LED, which vary depending on the hemoglobin concentration of the blood.

The sensors may also be designed to measure physical characteristics. For example, the sensors may be designed to measure pressure, acceleration or other physical characteristics.

According to embodiments of the present invention, the sensors shown in FIGS. 1-5 may be used in any order. For example, although the sensors 12a-12e shown in FIG. 1 may be a glucose/$pO_2$/temperature sensor; a lactate/$pO_2$/temperature sensor; a pH sensor; a potassium sensor; and an $SvO_2$ sensor, respectively, the order of the sensors 12a-12e may vary. Thus, each of the sensors may occupy any location within the interior of the housing 14.

Figure 6:
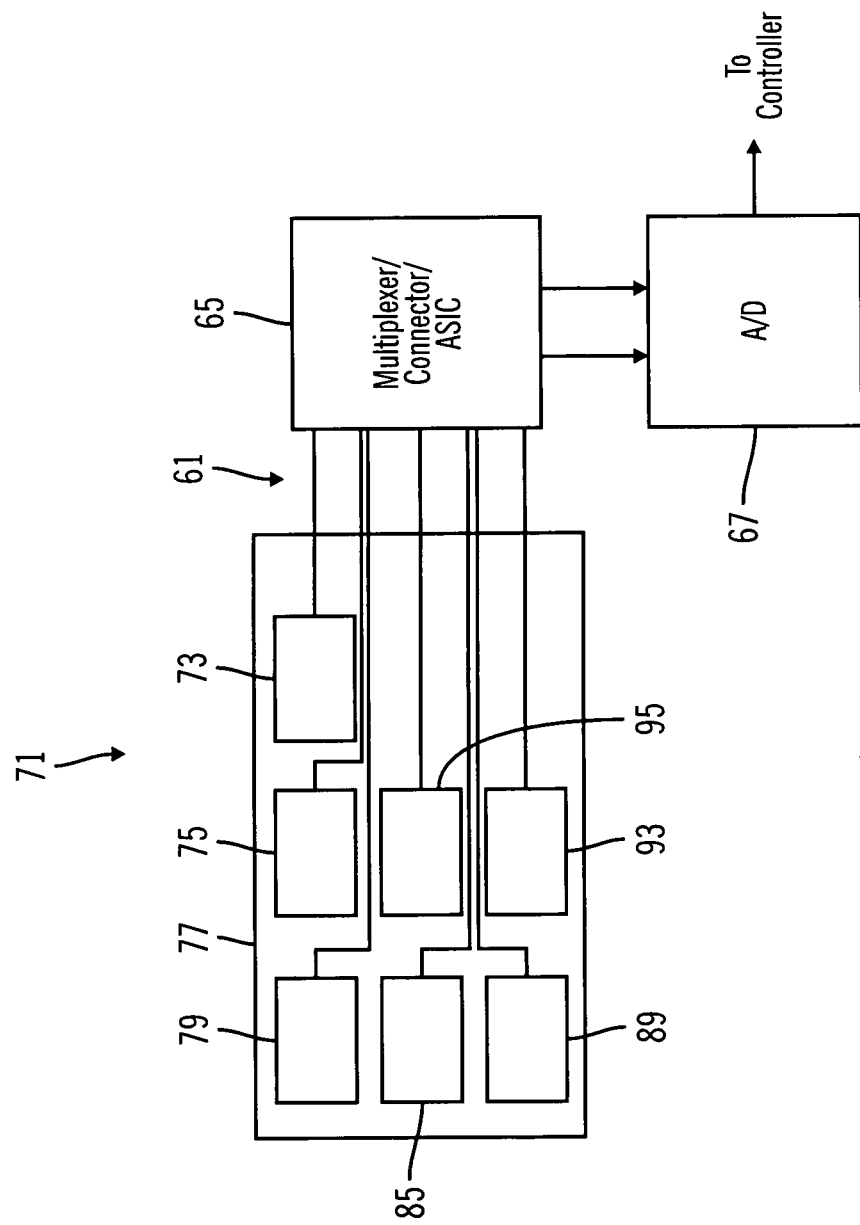
FIG. 6 shows a block diagram of a sensor system according to an embodiment of the present invention.

FIG. 6 shows an embodiment of a sensor system 71 that may be used in conjunction with embodiments of the present invention. The embodiment of the invention shown in FIG. 6 includes, but is not limited to, an electrode array 77, a multiplexer/controller/ASIC 65 and a digitizer or A/D 67. The electrode array 77 in the embodiment of the invention shown in FIG. 6 includes, without limitation, a glucose electrode 79, a lactate electrode 85, an oxygen electrode 89, a reference electrode 75, an enzyme counter electrode 95, an oxygen counter electrode 93 and a pressure transducer 73. However, embodiments of the present invention are not limited to the electrode array 77 or the pressure transducer 73 shown and other embodiments of the invention may include other electrodes and other transducers.

The electrode array 77 may be fabricated in a variety of ways. For example, according to one embodiment of the present invention, the electrode array 77 may be fabricated onto a standard silicon chip. The chip may have a width of approximately 700 microns and a length of approximately 6 cm. The chip may be fabricated by first depositing a metalization layer (e.g., chrome/gold/chrome) onto a silicon substrate. Next, the electrode array 77 and interconnects 61 for the glucose electrode 79, lactate electrode 85, oxygen electrode 89, reference electrode 75, enzyme counter electrode 95 and oxygen counter electrode 93 may then be defined and patterned using standard photoresist/stripping etching technology.

After the electrode array 77 and interconnects 61 have been defined and patterned, windows for the electrodes and insulation may then be defined and patterned using a photoimageable polyamide system. The pressure transducer 73 may be fabricated by micromachining a CMOS portion of a wafer using standard dry etch technology or other standard techniques. By monitoring a difference in capacitance between the CMOS portion and an offset reference pad and a thin, rigid silicon top member and the offset reference pad, local pressure may be determined. The rigid silicon top member may be implemented by any of a variety of methods that are well-known in the art.

The ASIC portion of the multiplexer/controller/ASIC 65 controls three potentiostat circuits, one for measuring oxygen by reduction electrochemistry, one to measure glucose by measuring hydrogen peroxide produced by glucose oxidase on the glucose electrode (i.e., by measuring the oxidation of $H_2O_2$), and one to measuring $H_2O_2$ made by lactose oxidase on the lactate sensor. The pressure transducer circuit measures a change in capacitance as the pressure of the cranial tissue increases.

According to another embodiment of the present invention, the sensor system 71 of FIG. 6 may be implemented using a single potentiostat in pulse mode to differentially and singly interrogate the oxygen, glucose and lactate sensors using chronoamperometry. This embodiment allows for a simplification of the associated electronic circuitry. In addition, this embodiment may display temporal data in real time for all analytes. Moreover, the electrode array may easily be extended to include other electrochemically measurable analytes, such as, for example, pyruvate, pH, $CO_2$, and electrochemically measurable neurotransmitters such as dopamine, for example.

Figure 7:
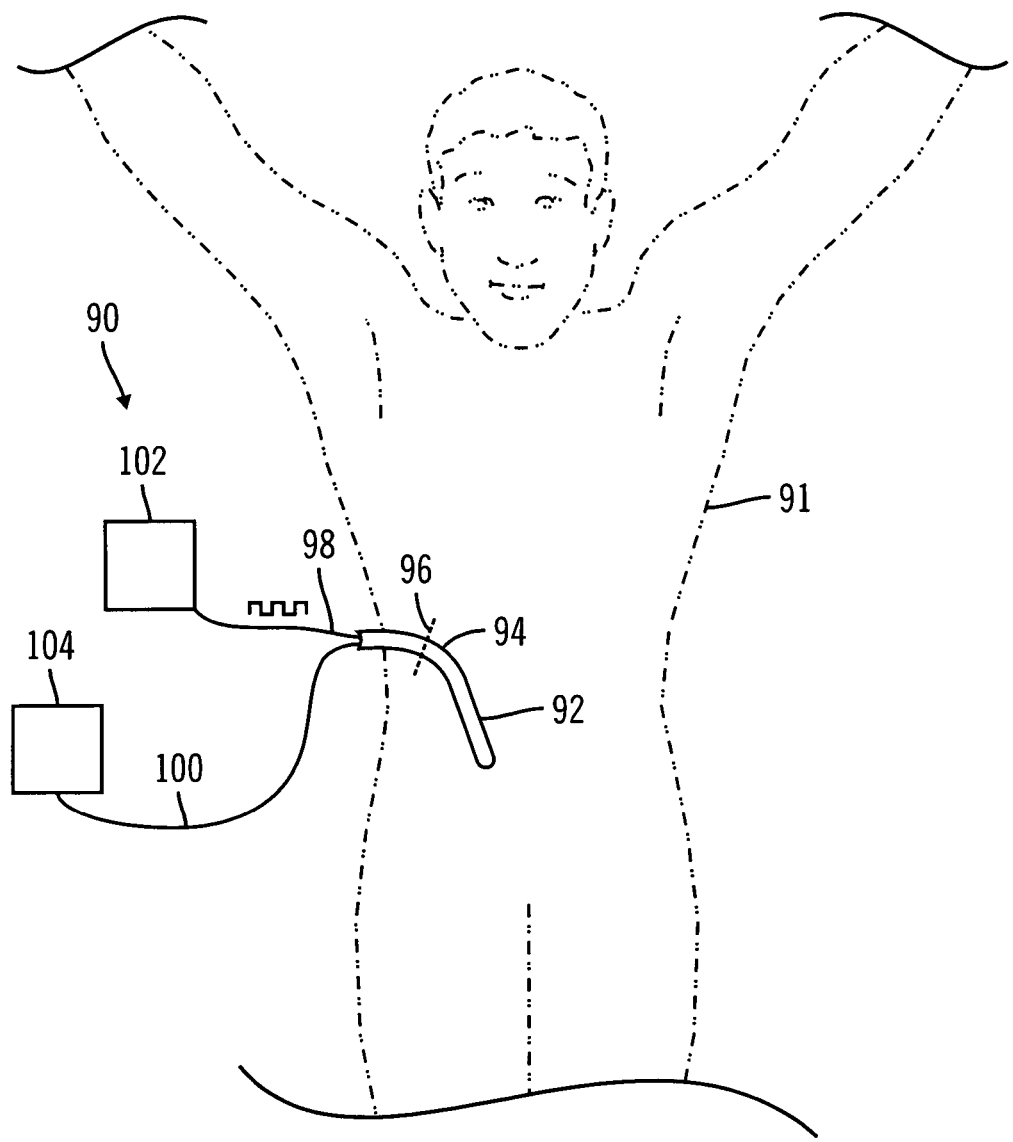
FIG. 7 shows a block diagram of an apparatus for sensing multiple parameters implanted in a patient according to an embodiment of the present invention.

A block diagram of a multi-parameter sensing system 90 with a multi-parameter sensor implanted in a patient may be seen in FIG. 7. In FIG. 7, an apparatus for sensing multiple parameters 92 is inserted into a patient 91. A catheter portion 94 of the apparatus for sensing multiple parameters 92 exits the patient 91 at an incision 96 and extends out of the patient 91. If the apparatus for sensing multiple parameters 92 shown in FIG. 7 is a daisy-chained apparatus, the information present on the interconnect 98 may be in digital form and may be connected directly to a computer 102 or other analytical device. The apparatus for sensing multiple parameters 92 in FIG. 7 may also include an infusion line 100 which may be connected to an infusant delivery system 104 or other delivery system.

Figure 8:
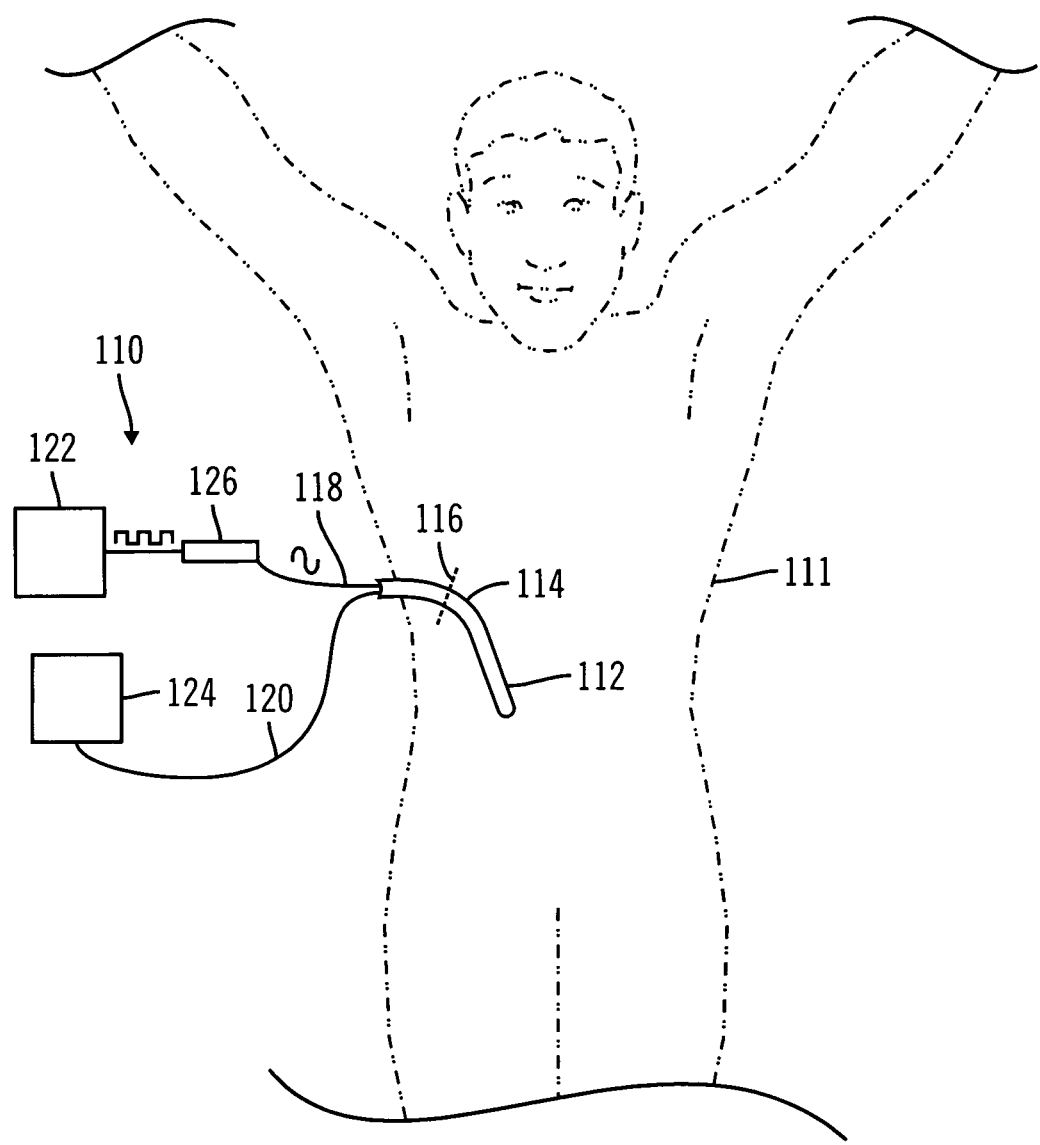
FIG. 8 shows a block diagram of another apparatus for sensing multiple parameters implanted in a patient according to an embodiment of the present invention.

A block diagram of a multi-parameter sensing system 110 according to another embodiment of present the present invention may be seen in FIG. 8. In FIG. 8, an apparatus for sensing multiple parameters 112 is implanted in a patient 111. A catheter portion 114 of the apparatus for sensing multiple parameters 112 exits the patient 111 at an incision 116 and extends out of the patient 111. In the embodiment of the invention shown in FIG. 8, if the apparatus for sensing multiple parameters 112 is a "wired" sensing apparatus, the information contained on the interconnect 118 may be in analog form. The interconnect 118, which may be a plurality of interconnects, may be connected to an analog-to-digital converter (A/D) 126. The information coming out of the A/D 126 is in digital form and may be connected to a computer 122 or other analytical device. According to another embodiment of the present invention, the information contained on the interconnect 118, being in analog form, may also be connected directly to an oscilloscope or other analytical device. The multi-parameter sensing system 110 may also include an infusion line 120 which may be connected to an infusant delivery system 124.

Figure 9:
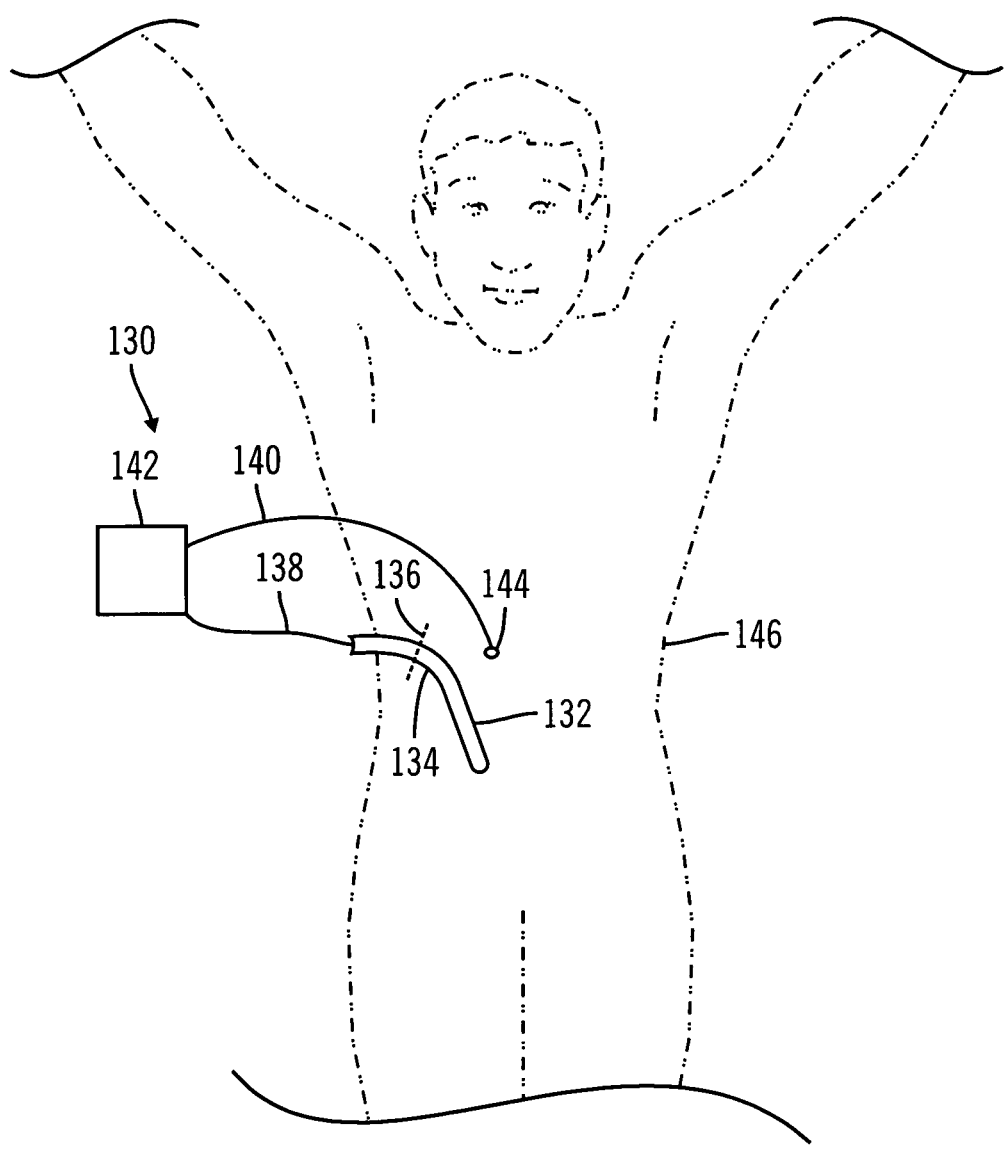
FIG. 9 shows a block diagram of another apparatus for sensing multiple parameters implanted in a patient according to an embodiment of the present invention.

A block diagram of a multi-parameter sensing system 130 according to another embodiment of present the present invention may be seen in FIG. 9. In FIG. 9, an apparatus for sensing multiple parameters 132 is implanted in a patient 146. A catheter portion 134 of the apparatus for sensing multiple parameters 132 exits the patient 146 at an incision 136 and extends out of the patient 146. In the embodiment of the invention shown in FIG. 9, one of the sensors in the apparatus for sensing multiple parameters 132 includes an internal electrode which cooperates with an external electrode 144. An first interconnect 138, which includes a signal from the internal electrode on one of the sensors in the apparatus for sensing multiple parameters 132, and a second interconnect 140 are connected to a computer or other controller/analyzer 142. The computer or other controller/analyzer 142 is able to sense a change of impedance between the internal electrode on one of the sensors in the apparatus for sensing multiple parameters 132 and the external electrode 144, corresponding to a change in the chemical, biological or physiological make-up of the area between the two electrodes, i.e., the patient.

For example, if a patient enters a state of edema, an increase in fluid in body tissue, the embodiment of the present invention shown in FIG. 9 could be used to detect the edema. An increase in fluid in body tissue may correspond to a change in the impedance of the body tissue, which would be sensed by the internal electrode and the external electrode 144.

Embodiments of the present invention may be advantageously used in a variety of ways. For example, severe sepsis and septic shock may be mitigated by using embodiments of the present invention. Severe sepsis and septic shock may be mitigated by continuously monitoring lactate levels in a patient. The concentration of lactate in the blood increases as a patient enters a septic phase. In addition, the concentration of blood potassium typically lowers as a patient enters a septic phase while central venous pressure drops. Also, according to some schools of thought, venous $O_2$ can rise as a patient becomes septic or is going through sepsis. Thus, embodiments of the present invention may be used to continuously monitor blood lactate, venous $O_2$, potassium and central venous pressure, thereby allowing a physician or other medical attendant to administer to the patient responsive treatment based on the monitored parameters and prevent the patient from becoming septic.

Embodiments of the present invention may also be used to maintain proper insulin levels, especially in diabetics. For example, according to an embodiment of the present invention, blood glucose may be monitored and insulin levels adjusted accordingly to prevent a patient from becoming hypoglycemic or hyperglycemic. Along with glucose, $O_2$ and temperature measurements may be made to assist the medical professional in determining the most advantageous time and manner to adjust the patient's insulin to the proper levels.

Embodiments of the present invention allow medical professionals to use one sensing apparatus to measure multiple parameters. As has been shown, a single sensing apparatus may be implanted at a single site in a patient. Moreover, a plurality of parameters may be read from the single apparatus implanted at the single site in the patient. Thus, the medical and surgical risks involved by placing multiple devices or sensors on a patient to measure desired parameters are reduced.

Embodiments of the present invention may be used in vascular or non-vascular applications. For example, sensors according to embodiments of the present invention be inserted into the vasculature. According to other embodiments of the present invention, sensors may be positioned in the peritoneal or may be positioned subcutaneously. Embodiments of the present invention may also be used for intracranial and defibrillation applications.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. An apparatus for sensing multiple parameters comprising:
   an implantable housing;
   an implantable tip affixed to a first end of the housing;
   a plurality of implantable sensors with sensing elements disposed within the implantable housing for sensing a plurality of different parameters in a patient;
   each sensor has a first surface on which the sensing element is disposed, the first surface extends along a plane;
   each sensor is arranged such that the plane in which the first surface of a sensor extends intersects with the plane in which the first surface of an adjacent sensor extends; and
   each sensor for detecting a different type of molecule relative to at least one other sensor in the plurality of implantable sensors.

2. The apparatus of claim 1, wherein the plurality of implantable sensing elements are biological parameter sensing elements.

3. The apparatus of claim 1, wherein the plurality of implantable sensing elements are physiological parameter sensing elements.

4. The apparatus of claim 1, wherein the plurality of implantable sensing elements are analyte sensing elements.

5. The apparatus of claim 1, wherein at least one of the plurality of sensing elements responds to blood oxygen saturation.

6. The apparatus of claim 1, further comprising an infusion line for delivering an infusion, the infusion line being disposed within the implantable housing and adjacent the plurality of sensing elements.

7. The apparatus of claim 1, wherein the plurality of implantable sensing elements are electrodes disposed on a substrate.

8. The apparatus of claim 7, wherein one of the electrodes is a glucose electrode.

9. The apparatus of claim 7, wherein one of the electrodes is a lactate electrode.

10. The apparatus of claim 7, wherein one of the electrodes is an oxygen electrode.

11. The apparatus of claim 7, wherein one of the electrodes is a reference electrode.

12. The apparatus of claim 7, wherein one of the electrodes is an enzyme counter electrode.

13. The apparatus of claim 7, wherein one of the electrodes is an oxygen counter electrode.

14. The apparatus of claim 1, wherein the plurality of implantable sensing elements includes a pressure transducer.

15. The apparatus of claim 1, wherein the plurality of implantable sensing elements sense intracranial parameters.

16. The apparatus of claim 1, wherein at least one of the implantable sensing elements responds to lactate.

17. The apparatus for sensing multiple parameters of claim 1, wherein the plurality of implantable sensors further comprising an oxygen sensor and a glucose sensor wherein the plurality of implantable sensors are operatively coupled to a single potentiostat to differentially and individually interrogate oxygen, glucose and lactate.

18. The apparatus for sensing multiple parameters of claim 17, wherein the plurality of implantable sensors are configured to generate signals that include temporal data in real time for a plurality of sensed parameters.

19. The apparatus of claim 1, wherein each sensor is arranged such that the plane in which the first surface of a sensor extends is perpendicular to the plane in which the first surface of an adjacent sensor extends.

20. An apparatus for sensing multiple parameters comprising:
   an implantable housing;
   an implantable tip affixed to a first end of the housing;
   a plurality of implantable sensors disposed within the implantable housing for sensing a plurality of different parameters in a patient; each sensor comprising a plurality of sensing elements, the plurality of sensing elements disposed on a single sensor, each sensing element configured to detect a different type of molecule relative to at least one other sensing element in the plurality of sensing elements and
   wherein at least one of the plurality of sensing elements is configured to use lactate oxidase enzyme that responds to lactate;
   wherein the plurality of sensing elements further comprise an oxygen sensing element and a glucose sensing element wherein the plurality of sensing elements are operatively coupled to a single potentiostat to differentially and individually interrogate oxygen, glucose and lactate.

21. The apparatus for sensing multiple parameters of claim 20, wherein the plurality of sensors are configured to generate signals that include temporal data in real time for a plurality of sensed parameters.

22. The apparatus of claim 20, wherein each sensing element comprises at least two electrodes.

23. The apparatus of claim 20, wherein the plurality of sensing elements are disposed on a single silicon chip.

24. The apparatus of claim 23, wherein the single potentiostat is used in pulsed mode using chronoamperometery.

* * * * *